United States Patent [19]
Welkowitz et al.

[11] Patent Number: 5,101,828
[45] Date of Patent: Apr. 7, 1992

[54] METHODS AND APPARATUS FOR NONIVASIVE MONITORING OF DYNAMIC CARDIAC PERFORMANCE

[75] Inventors: Walter Welkowitz, Metuchen; Qing Cui, Highland Park; Yun Qi, Piscataway, all of N.J.

[73] Assignee: Rutgers, The State University of NJ, New Brunswick, N.J.

[21] Appl. No.: 685,591

[22] Filed: Apr. 11, 1991

[51] Int. Cl.[5] .............................................. A61B 5/02
[52] U.S. Cl. ................................... 128/668; 128/687; 128/691; 364/413.05
[58] Field of Search .............. 128/687, 668, 691, 702, 128/661.08; 364/413.02–413.06

[56] References Cited
U.S. PATENT DOCUMENTS

| | | | |
|---|---|---|---|
| 4,860,759 | 8/1989 | Kahn et al. | 128/668 |
| 4,989,611 | 2/1991 | Zauetti et al. | 128/687 |
| 4,993,420 | 2/1991 | Welkowitz et al. | 128/668 |
| 5,033,472 | 7/1991 | Sato et al. | 128/691 |

Primary Examiner—Francis Jaworski
Assistant Examiner—George Manuel

[57] ABSTRACT

Apparatus for noninvasively monitoring cardiovascular system parameters of a living subject comprises means for sensing waveforms externally of the body of the subject above the carotid and femoral arteries, means for non-invasively calibrating and digitizing the pulse waveforms, and a digital signal processor having means for converting the digitized, calibrated pulse information by Fast Fourier Transform to first and second sets of harmonically related blood pressure components in the frequency domain, means for comparing corresponding ones of the components in the first and second harmonically related sets to determine amplitude and phase transfer function components of the portion of the cardiovascular system between the carotid and femoral arteries, means for simulating the portion of the system by a hybrid electrical circuit model having at least three variable parameters, means for determining corresponding amplitude and phase transfer function components of the hybrid model and for adjusting the variable parameters so as to substantially match the transfer functions of the model and the portion of the cardiovascular system, and means for determining cardiac output utilizing the adjusted parameters of the hybrid model and the calibrated pulse information.

16 Claims, 14 Drawing Sheets

*CALIBRATION FOR PATIENT*

FLOWCHART OF *INTRODUCTION*

FLOWCHART OF *CALIBRATION*

FLOWCHART OF *SAMPLING*

FLOWCHART OF SELECTION

FLOWCHART OF *SETTING UP PARAMETERS*

FIG. 11   BLOCK DIAGRAM OF OPTIMIZATION PROCEDURE

COMPUTER FLOW DIAGRAM FOR
THREE-FIGURE-OF-MERIT OPTIMIZATION

BASIC STRUCTURE OF THE PARAMETER
DETERMINATION COMPUTER PROGRAM

SIMPLIFIED FLOW DIAGRAM FOR THE OPTIMIZATION STRATEGY "OPSD"

SIMPLIFIED FLOW DIAGRAM
OF SUBROUTINE "TRICK"

METHODS AND APPARATUS FOR NONINVASIVE MONITORING OF DYNAMIC CARDIAC PERFORMANCE

RELATED APPLICATION

This application is related to the subject matter of U.S. Pat. No. 4,993,420, based on U.S. Patent Application Ser. No. 07/502,409, filed Mar. 30, 1990 in the names of Walter Welkowitz, Qing Cui and Yun Qi entitled "Method and Apparatus for Noninvasive Monitoring Dynamic Cardiac Performance", which was granted Feb. 19, 1991.

BACKGROUND OF THE INVENTION

This invention relates to improved methods and apparatus for noninvasively monitoring dynamic cardiac performance of a living subject.

Cardiac output is an important parameter of the circulatory system since it is a direct measure of systemic blood flow and thereby the transport of oxygen and nutrients to all tissues of the body. Heart disease can result in a decrease of cardiac output leading to inadequate nutrition of the cells of the body. Therefore, measuring cardiac output is useful in monitoring the critically ill patient, in rehabilitation medicine and in medical screening procedures.

The most common methods of measuring blood flow used at this time are invasive and are therefore not suitable for many patients and circumstances. A simple to use, noninvasive apparatus to measure or accurately estimate cardiac output could be applied to all patients.

Cardiac output may be expressed as the product of heart rate and volume of blood pumped per beat of the heart. Thus, under conditions of a consistent heart rate and stroke volume, Cardiac Output = (Heart Rate) (Stroke Volume)

$$\frac{\text{Liters}}{\text{Min}} = \frac{\text{Beats}}{\text{Min}} \times \frac{\text{Liters}}{\text{Beat}}$$

Cardiac output or blood flow is also directly proportional to mean blood pressure and is inversely proportional to the peripheral resistance of the arterial system through which the blood flows (i.e. the aorta).

Because of the importance of changes in cardiac output and the difficulties in its direct measurement, the estimation of cardiac output and stroke volume from blood pressure pulse waveforms has been extensively studied (see "Engineering Hemodynamics: Applications to Cardiac Assist Devices" by Walter Welkowitz, first published by D. C. Heath & Co., First Ed. 1977; Second Ed. NYU Press, 1987).

In one approach, McDonald (1974) recorded two pressure pulses 3-5 cm apart within the ascending aorta (an invasive technique). Both pulses were subjected to Fourier analysis and the apparent phase velocity was calculated for each harmonic of the pulses. The phase velocities were applied to the Wormsley equation to calculate aortic flow and stroke volume (the integral of aortic flow throughout one cycle). A problem encountered with this method is that the aorta exhibits nonuniform geometric and elastic properties and thereby renders the Wormsley calculation inaccurate. To overcome that problem, Muthukrishnan and Jaron (1975) used a parameter optimization technique to compute aortic input impedance in a manner similar to an earlier proposal of Strano, Welkowitz and Fich (1972) based upon an aorta model developed still earlier by Welkowitz and Fich (1967). Instantaneous aorta flow waveforms were calculated by Muthukrishnan from the input impedance and the proximal aortic pressure. The aortic flow waveform estimated by this analysis closely matched an actual flow waveform measured using a electromagnetic flow meter. The Muthukrishnan method, however, which is based upon two internal pressure measurements, is an invasive stroke volume technique.

Min, Welkowitz and Kostis (in 1978) described an extension of this technique using two simultaneous noninvasive pulse contour measurements acquired with two piezoresistive pulse transducers combined with an ultrasonic measurement of aortic diameter (see Proc. 6th New England Bioengineering Conference. pp. 15-19). In addition to the foregoing pressure and pulse techniques, there has been a great deal of work in the areas of doppler ultrasound and bioimpedance measurements (see U.S. Pat. No. 4,562,843—Djordjevich et al.; Welkowitz et al., "Biomedical Instruments: Theory and Design", Academic Press, New York, 1976; Kubicek et al., "Impedance Cardiography as a Non-invasive Method of Monitoring Cardiac Function and other Parameters of the Cardiovascular System", Ann. N.Y. Acad. Sci., 170: 724, 1970).

It is known that hemodynamic characteristics of the aorta can be simulated by an R-L-C electrical linear network. Researchers have developed various aorta simulation models to perform estimations and calculations for different purposes. Based upon an equivalent electrical circuit model developed by Watts (1974), an aortic flow waveform has been calculated from a carotid pulse waveform. A corresponding cardiac output then may be computed. A microcomputer can be used for this simulation and calculation.

The knowledge that the aorta can be represented by an electrical circuit model has led some researchers to seek a noninvasive method and apparatus for cardiac output monitoring using circuit simulation. One such modeling technique is described in our above-referenced Application Ser. No. 07/502,409, the disclosure of which is herein incorporated by reference.

SUMMARY OF THE INVENTION

In a method according to the present invention, the aorta is simulated by a hybrid electrical circuit model. The transfer function (phase and amplitude response as a function of frequency) of the hybrid circuit model is represented by equations having four unknown parameters (see Strano, Welkowitz and Fich, "Cost Function Analysis Applied to the Determination of Aorta Parameters", Int. J. Engn. Science 10: 1081-1091, 1972 for definitions of the aorta taper coefficient K, the effective resistance per unit length R, the effective capacitance per unit length C and the blood inertance L). The transfer function is set up for an iterative calculation on a standard desktop computer (e.g., PC), utilizing various combinations of values for three of the four parameters. Blood inertance is assumed to be a constant (which is a practical assumption). Simultaneous pulse contour waveforms are sensed on the outside of the body of a living subject above the carotid artery and above the femoral artery. The two pulse waveforms are converted by a Fast Fourier Transform (FFT) procedure to harmonically related frequency components. The carotid and femoral FFT components are compared to derive phase and amplitude components of the transfer function of the intervening arterial system. These measured transfer function components are then compared to the corresponding transfer function components of the hybrid circuit model and the parameters of the hybrid circuit model are adjusted by means of a matching optimization program until an acceptable match is obtained between the transfer function of the model and the transfer function determined by the measurements made on the subject.

The sensed pulse waveforms, which initially are uncalibrated, are converted to pressure information prior to the FFT step, for example, by information obtained from a noninvasive, external systolic/diastolic arm cuff measurement of the subject. The measured pressure values are correlated with the waveform voltages at the peak and minimum points of the carotid pulse waveform. The femoral waveform calibration is obtained by utilizing the measured diastolic pressure as the femoral waveform minimum and the measured systolic pressure multiplied by a predetermined factor (e.g., 1.06) for the femoral waveform maximum. Appropriate voltage to pressure coefficients are calculated and are used thereafter to convert the sensed electrical waveform amplitudes to pressure values.

More specifically, in a method according to the invention, a carotid pulse is sensed and is converted to a carotid pulse electrical voltage waveform and, simultaneously, a femoral pulse is sensed and is converted to a femoral pulse electrical voltage waveform. Both electrical voltage waveforms are digitized. The digitized pulse waveforms are calibrated as to amplitude and are subjected to the Fast Fourier Transform analysis (i.e., converted to harmonically related frequency components). Amplitude and phase comparisons are made for each pair (carotid and femoral) of frequency components to derive measured phase and amplitude transfer functions for the subject. The parameters of a hybrid mathematical model of the aorta are adapted to be varied automatically by means of a matching optimization program stored in a computer. The parameters of the model are adjusted and corresponding transfer function components are calculated and compared to the measured transfer function of the subject after each adjustment until the best match of the measured and calculated transfer functions is obtained. The model is then considered to be representative of the aorta of the living subject and the final values of the four parameters are utilized to calculate the input impedance of the optimized model. Aortic flow is calculated from the impedance parameter of the model and the calibrated, measured carotid pressure information of the subject. The aortic flow information is then converted to the time domain by Inverse Fast Fourier Transform techniques and the time integral of the transformed flow information is calculated to provide stroke volume. Cardiac output is then calculated by multiplying measured heart rate by the calculated stroke volume.

The system according to the invention makes use of two piezoelectric pulse transducers which are used to sense the carotid and femoral pulse waveforms.

BRIEF DESCRIPTION OF THE DRAWINGS

Methods and apparatus for cardiac output monitoring according to the present invention will be better understood from the following description, claims and appended drawings in which:

DESCRIPTION OF THE PREFERRED EMBODIMENT

Figure 1:
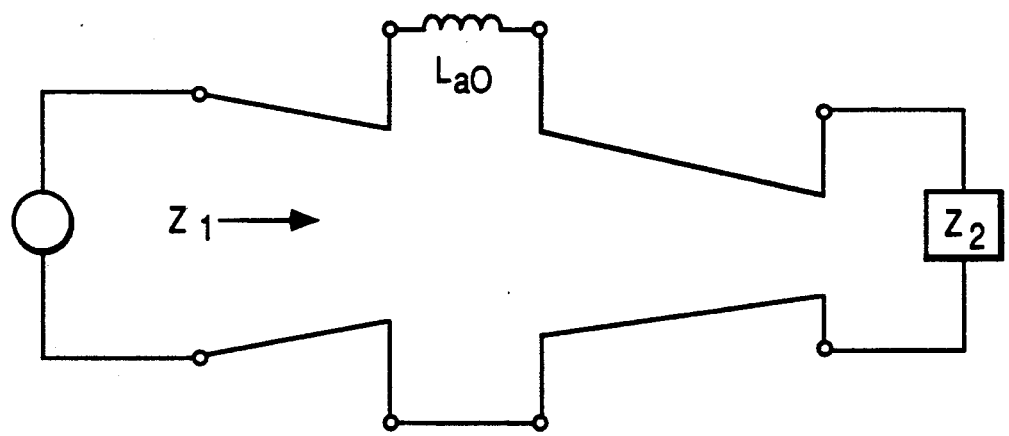
FIG. 1 is a diagram of a basic electrical hybrid model of an aorta.

In the model shown in FIG. 1, the geometric taper and non-uniform elasticity of the aorta are taken into account in the hybrid network which consists of distributed segments analogous to the elasticity, area, viscosity and viscoelasticity of the system and a lumped inertance representative of the blood in the aorta.

Stated in very general terms, the method to be described below employs the steps of externally sensing two pulse contours (time varying waveforms) at two extreme points along the aorta, calibrating the waveforms by means of a non-invasive pressure measurement and thereafter determining a frequency domain transfer function defined by the ratio of those two waveforms. The parameters of a hybrid model of the aorta are varied automatically and resulting transfer functions of the model and the measured subject are compared. The model parameters are changed until the transfer function of the model (both phase and amplitude parameters) is optimally matched to the measured transfer function of the subject. The input impedance of the model of the subject's aorta is then determined, utilizing the values of the parameters of the model arrived at in the foregoing matching process. The cardiac output (total aortic blood flow) then may be determined from the relationships among input impedance, input (carotid) pressure, aortic flow and pulse rate.

Figure 2:
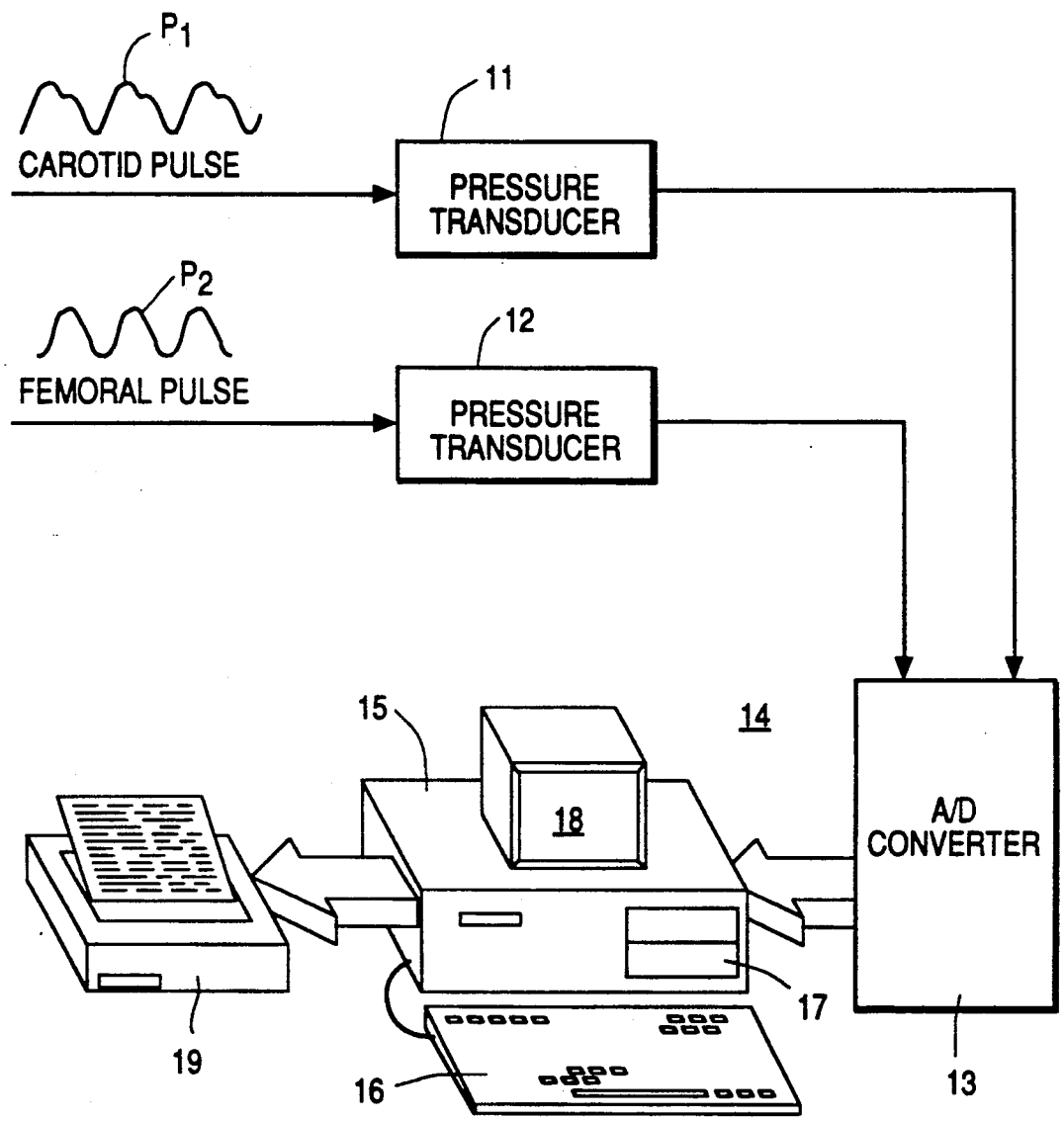
FIG. 2 is a diagrammatic block diagram of apparatus constructed according to the invention.
Figure 3:
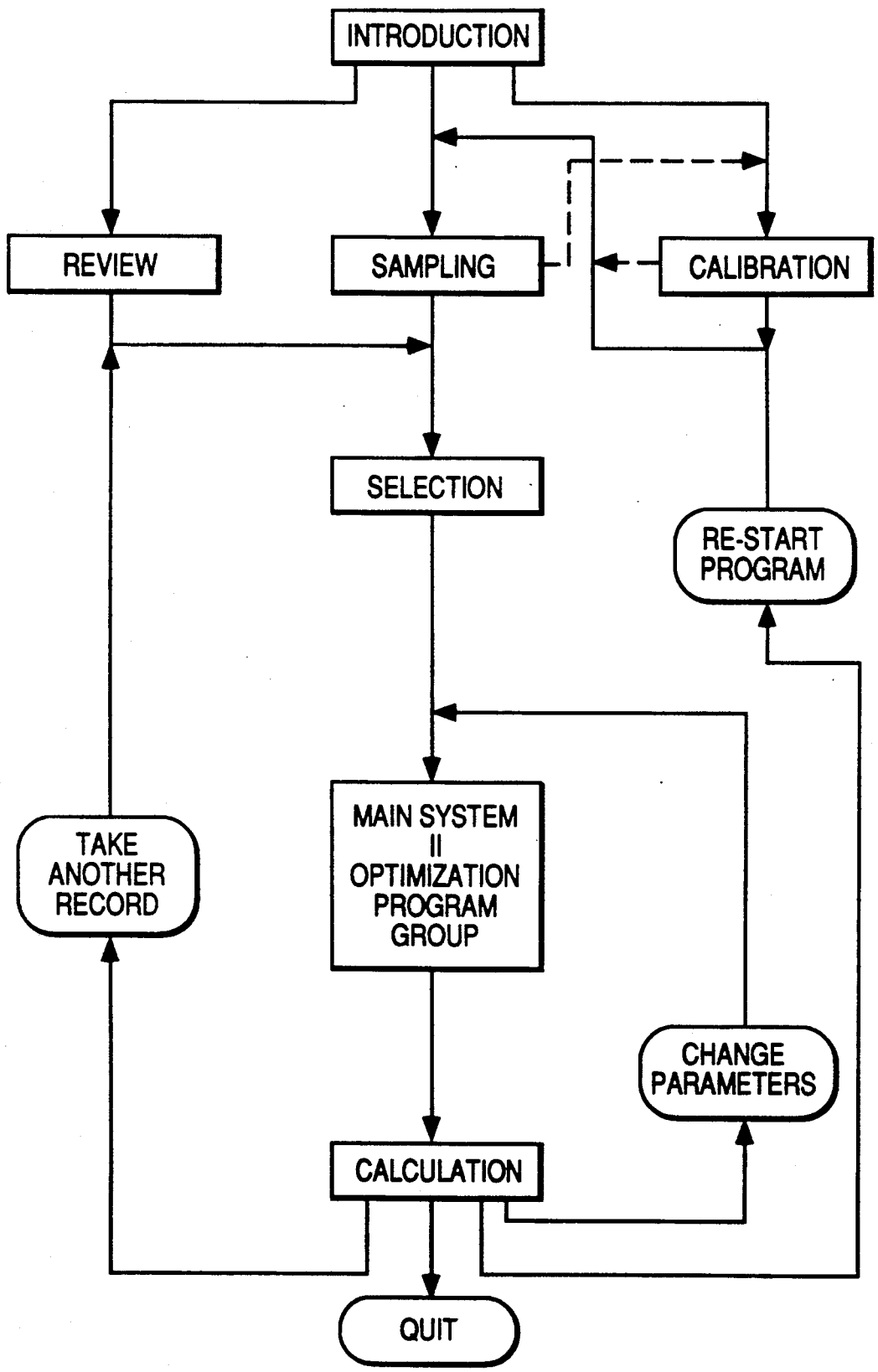
FIG. 3 is a diagram of a set of computer program routines useful in the invention.

As is shown in FIG. 2, a system for carrying out a method according to the invention comprises first and second noninvasive pulse transducers 11, 12 for converting externally sensed blood pressure perturbations to correspondingly shaped time-varying electrical voltage waveforms. The pulse output waveforms of transducers 11, 12 are coupled to an analog to digital (A/D) converter 13 where they are digitized (i.e., the analog waveforms are sampled at an appropriate sampling rate and the sampled amplitudes are converted, for example, to four bit digital numerical values). Pulse transducers 11, 12 preferably are adapted to be placed over a subject's carotid artery and femoral artery, respectively, in close contact with the subject's skin.

The digitized signal outputs from A/D converter 13 are supplied to a computer 14 (such as an IBM PC or equivalent) for processing as will appear below. Computer 14 typically includes a processor 15, a keyboard 16, a magnetic media storage device and drive 17, a visual display screen 18 and an associated graphics printer 19.

The pulse transducers 11, 12 preferably are of a piezoelectric transducer type and provide output signals to appropriate filter/amplifier circuits (not shown) suitable for interfacing with A/D converter 13. It should be recognized that the proper positioning of the pulse transducers 11, 12 requires knowledge of the location of the carotid and femoral arteries. However, by providing the visual display screen 18 in connection with computer 14 (as is customary), it is possible for a health care professional to position the transducers 11, 12 and, by observing the appropriate position which results in substantially maximum pulse waveforms appearing on the display screen 18, to produce repeatable and acceptable output signals from transducers 11, 12.

It should be noted that the output waveforms, upon being sensed by transducers 11, 12 are not calibrated in terms of pressure. In order to provide such calibration, noninvasive measurements of systolic and diastolic pressures of a subject are made. It has been determined experimentally that a sufficiently accurate amplitude calibration of the transducer outputs may be provided making use of a pressure cuff sphygmomanometer as will be explained in more detail below. Other external pressure measuring devices of similar or greater accuracy may also be employed for this purpose.

According to one aspect of the present invention, after the pressure waveforms are sensed and digitized, the following sequence of signal processing takes place within computer 14, with the ultimate objective of measuring total cardiac output (blood flow) of the subject.

The aorta is simulated by a non-uniform, hybrid electrical network model as illustrated in FIG. 1 (see Welkowitz, "Engineering Hemodynamics", referenced above, at Page 40 and following). If $P_1$ represents the time varying waveform of the carotid pulse (see FIG. 2) and $P_2$ represents the time varying waveform of the femoral pulse (see FIG. 2), in a method according to the invention, by calibrating the two pulse waveforms and converting the resulting information to the frequency domain by Fast Fourier Transform methods, the pressure transfer function $T_p$ for the aorta of the subject is determined by comparing the individual frequency components of the two measured pressure waveforms. Thereafter, making use of the equation for the hybrid model described in the Welkowitz treatise:

$$T_p = \frac{P_1(s)}{P_2(s)} = F_1(\gamma l_a) + F_2(\gamma l_a) + F_3(\gamma l_a) + F_4(\gamma l_a) + F_5(\gamma l_a) + F_6(\gamma l_a)$$

where $$F_1(\gamma l_a) = e^{-2kl_a}[\cosh \gamma l_a + (k/\gamma) \sinh \gamma l_a]^2$$

$$F_2(\gamma l_a) = (sR_a C_a/\gamma^2)(e^{-2kl_a} \sinh^2 \gamma l_a)$$

$$F_3(\gamma l_a) = \frac{s^2 l_a C_a}{\gamma}\left[e^{-2kl_a} \sinh \gamma l_a \left(\cosh \gamma l_a - \frac{k}{\gamma} \sinh \gamma l_a\right)\right]$$

$$F_4(\gamma l_a) = \frac{\gamma - k}{\gamma^2}\left[e^{-2kl_a} \sinh \gamma l_a \left(\cosh \gamma l_a - \frac{k}{\gamma} \sinh \gamma l_a\right)\right]$$

$$F_5(\gamma l_a) = \frac{\gamma - k}{\gamma^2} e^{-2kl_a} \sinh \gamma l_a (\cosh \gamma l_a - k \sinh \gamma l_a)$$

$$F_6(\gamma l_a) = \frac{sL_{a0}(\gamma - k)e^{-2kl_a}}{\gamma R_a}(\cosh \gamma l_a + k \sinh \gamma l_a)(\gamma \cosh \gamma l_a - k \sinh \gamma l_a)$$

and setting the parameters $l_a$ (aorta length) and $L_{ao}$ (blood inertance) equal to predetermined constant values, (e.g., 0.4 meters and $1.35 \times 10^6$ kg, respectively,) the remaining variable parameters $R_a$, $C_a$ and K of the hybrid model are adjusted making use of computer 14 and an appropriate error optimization program (see FIGS. 10-15, to "match" the pressure transfer function of the model with the pressure transfer function of the aorta of the subject. The final values of the parameters of the model are then determined and, preferably, are read out as well as being stored in computer 14.

After determining the parameters of the model, the equivalent flow waveform of the optimized model is determined from the relationship that flow is equal to aorta input pressure divided by the input impedance of the model. The input impedance ($Z_1$) is calculated making use of the model parameters and the relationships $$Z_1(j\omega) = \frac{\gamma R_a e^{(\gamma + k)l_a} + \frac{j\omega L_{a0}}{2}(\gamma - k)^2 - \frac{L_{a0} R_a C_a}{2}\omega^2 e^{\gamma l_a}}{(\gamma - k)\left[\gamma e^{(\gamma + k)l_a} - \frac{L_{a0} C_a}{2}\omega^2(e^{\gamma l_a} - 1)\right]};$$

and $$\gamma = (k^2 + sR_a C_a)^{\frac{1}{2}}$$

The aortic flow is then determined, recorded and processed (integrated and multiplied by pulse rate) to yield equivalent cardiac output.

The software used in implementing the invention is made up of a group of programs or routines which are, for example, written in BASIC. Certain of the programs such as the Fast Fourier Transform (FFT) program and the inverse FFT program are commercially available from numerous sources and are well known.

The overall system is designed to be "user friendly" for meeting the needs of operators, such as physicians or clinicians, who may not be familiar with computers. Following instructions step by step, they can manage the operations and obtain the desired results.

Figure 4:
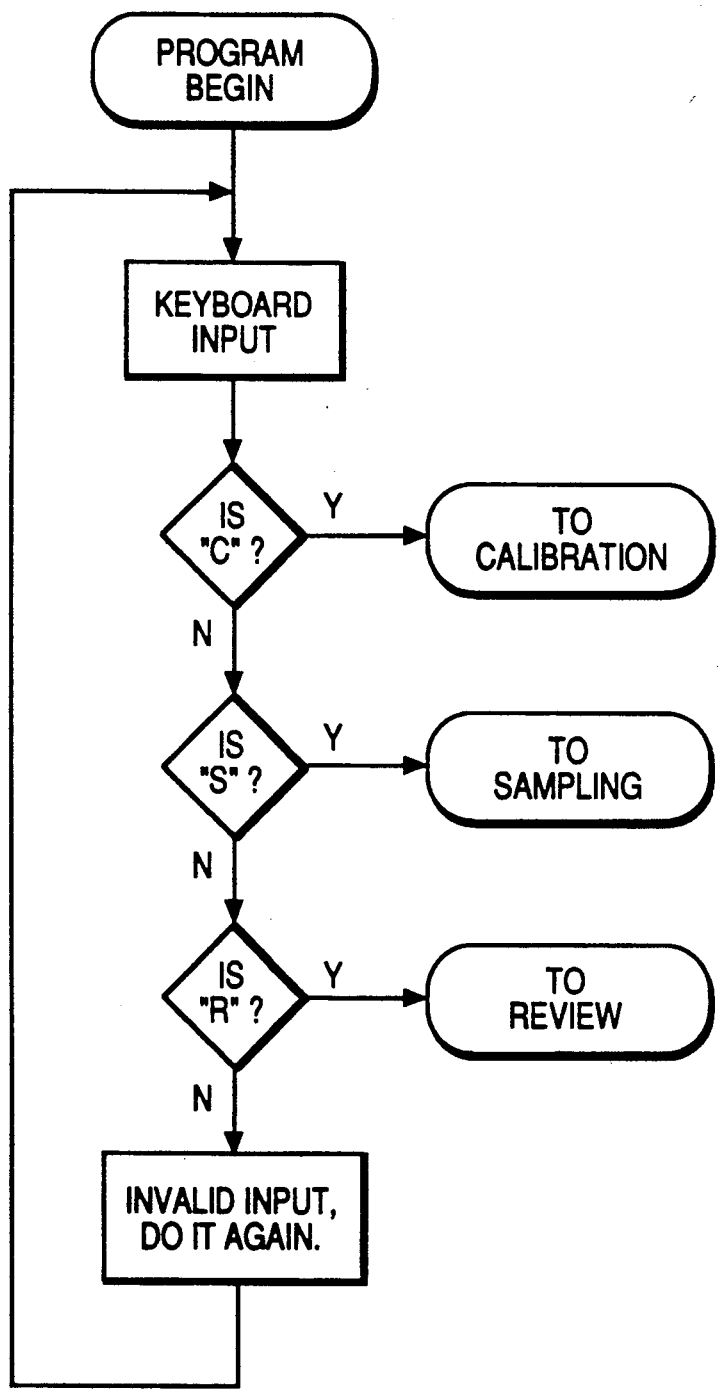
FIG. 4 is a flowchart of an INTRODUCTION routine used in this invention.

An INTRODUCTION routine introduces a user to the system and allows for choosing among three subroutines. Specifically, as shown in the INTRODUCTION routine flowchart in FIG. 4, depressing the letter "C" on keyboard 16 allows a user to initiate a CALIBRATION routine, depressing the letter "S" allows a user to initiate a SAMPLING routine and depressing the letter "R" allows a user to initiate a REVIEW routine.

Figure 6:
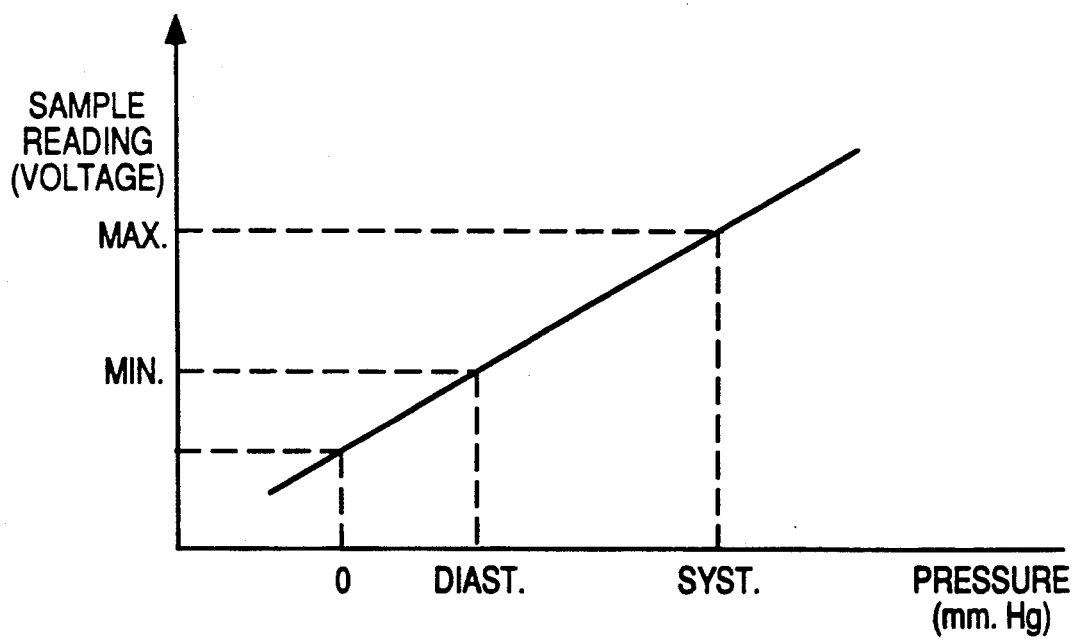
FIG. 6 illustrates relationships employed in calibration of waveforms for a subject.
Figure 5:
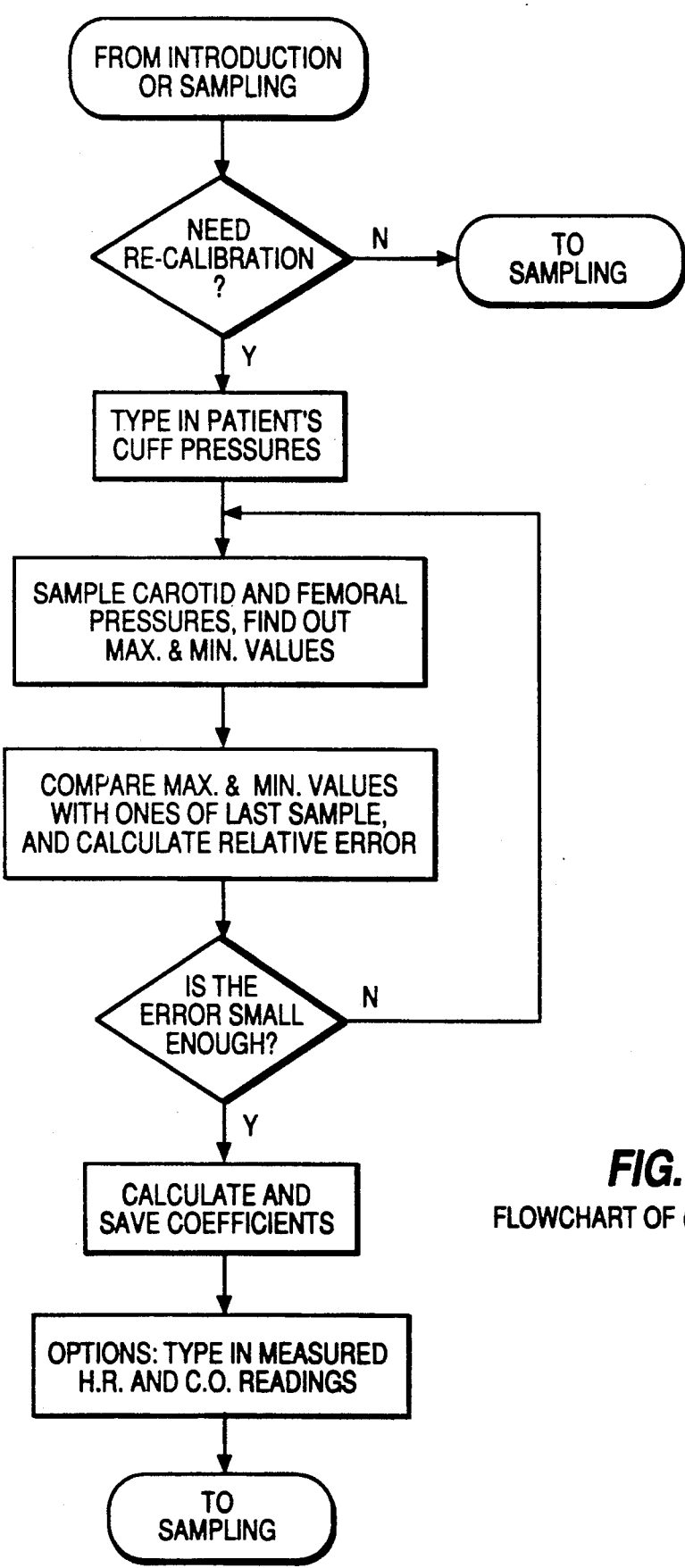
FIG. 5 is a flowchart of a CALIBRATION routine.

The CALIBRATION routine allows a user to calibrate the amplitude of the carotid and femoral pulse input waveforms by selecting appropriate pressure/voltage coefficients to be associated with these waveforms. Specifically, the coefficients are the slope and offset of a pressure versus voltage characteristic associated with the maximum and minimum of the sensed waveforms and the corresponding measured cuff pressures, as shown in FIG. 6. Calibration is based upon the cuff pressure readings (Systolic and Diastolic readings) measured from a subject during the taking of data. FIG. 5 shows a flowchart for the CALIBRATION routine. The calibration procedure compensates for the uncertainties in the location of transducers 11 and 12 with respect to the arteries, the variations from patient to patient in the tissue between the arteries and the transducers, as well as the varying electrical characteristics from transducer to transducer.

As shown in FIG. 5, at the beginning of the CALIBRATION routine, it is necessary first to determine whether or not a new calibration is required.

The user determines whether re-calibration is required. If the answer is no ("N"), then the CALIBRATION routine is exited, the SAMPLING routine is entered and, the existing calibration coefficients remain unchanged. If the answer is yes ("Y"), then the carotid pulse waveform maximum and minimum voltage levels are determined for a single pulse and those voltage values are compared with results from the corresponding samples taken during a preceding time interval. When the error between two such sets of samples is small enough, such as 1%, the waveforms are considered sufficiently reliable and new coefficients are calculated. Typically, the calculated coefficients are then saved in a file (the original contents are replaced). Upon completion of the CALIBRATION routine, the SAMPLING routine is entered.

Figure 7:
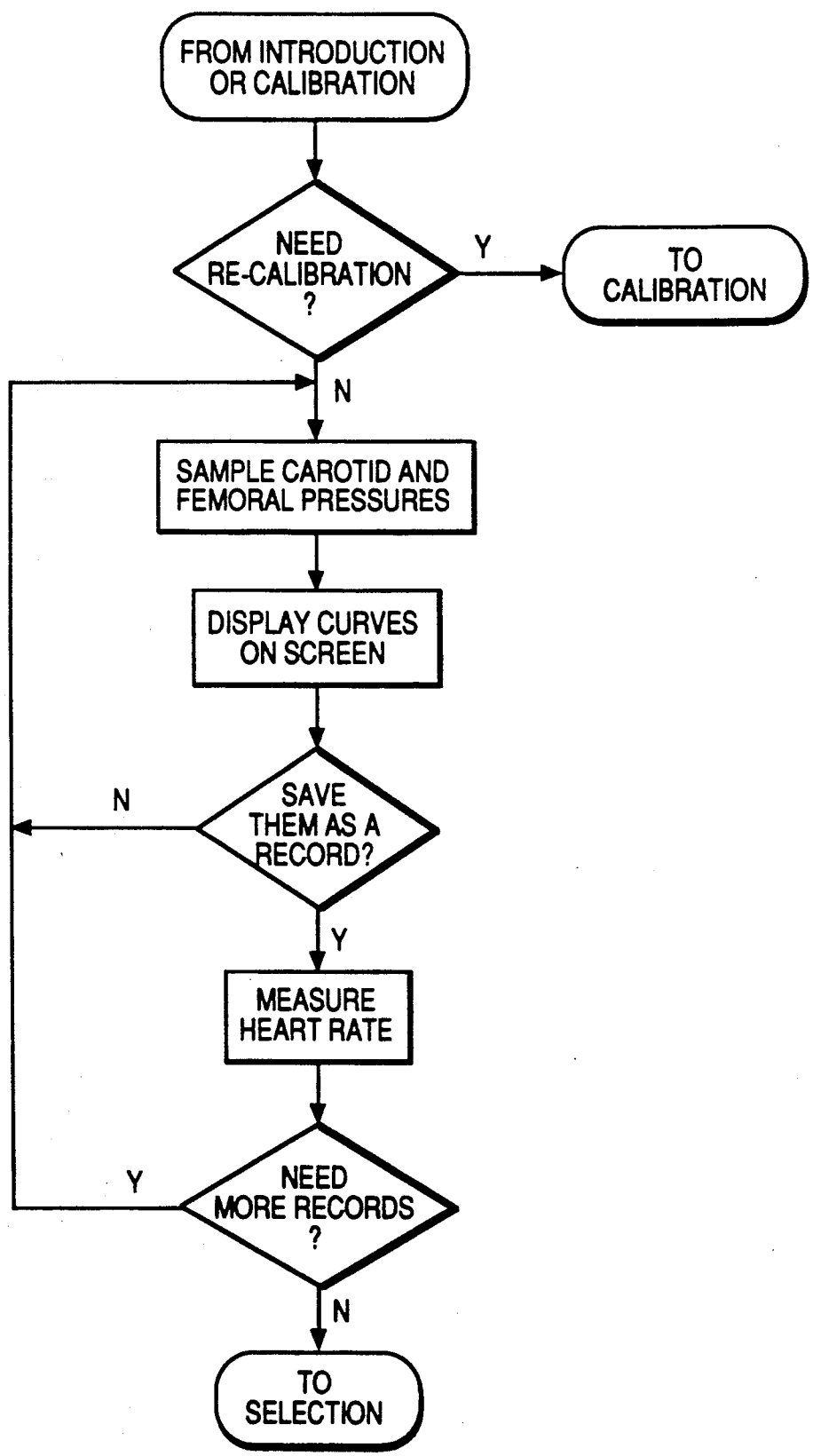
FIG. 7 is a flowchart of a SAMPLING routine.

The SAMPLING routine allows a user to reject a sample or to save a sample in memory so that only samples which are considered to be acceptable are saved. The flowchart of the SAMPLING routine is shown in FIG. 7. Similar to the CALIBRATION routine, a user is given the opportunity to recalibrate the signals. If a user chooses to recalibrate ("Y"), the system returns to the CALIBRATION routine. If a user chooses not to recalibrate ("N"), the original coefficients are maintained for the carotid pressure and femoral pressure information. That information is then digitized by the A/D converter 13 and is processed further.

When a pulse waveform is sensed by one of transducers 11, 12, that waveform may be displayed on screen 18. The user is prompted as to whether or not to save the sample waveform as a record. If the user chooses not to save the sample, that sample will be ignored and the sampling process will continue. If the user chooses to save the sample as a record, then the heart rate may also be measured from the waveforms displayed on the screen 18. Preferably, the operator measures heart rate by moving two arrow-like cursors left and right on the screen 18 using appropriate keys on keyboard 16. The positioning of the cursors in this manner serves to measure an entire period of the heart beat and to allow computation of the heart rate. A proper or reasonable range of heart rate, for example, less than 200 and greater than 30, can be established in the system, so that data outside this range will not be taken into account.

When the SAMPLING routine is finished, records are saved in memory 17.

The SELECTION routine allows a user to select a set of input signals (a record).

Figure 8:
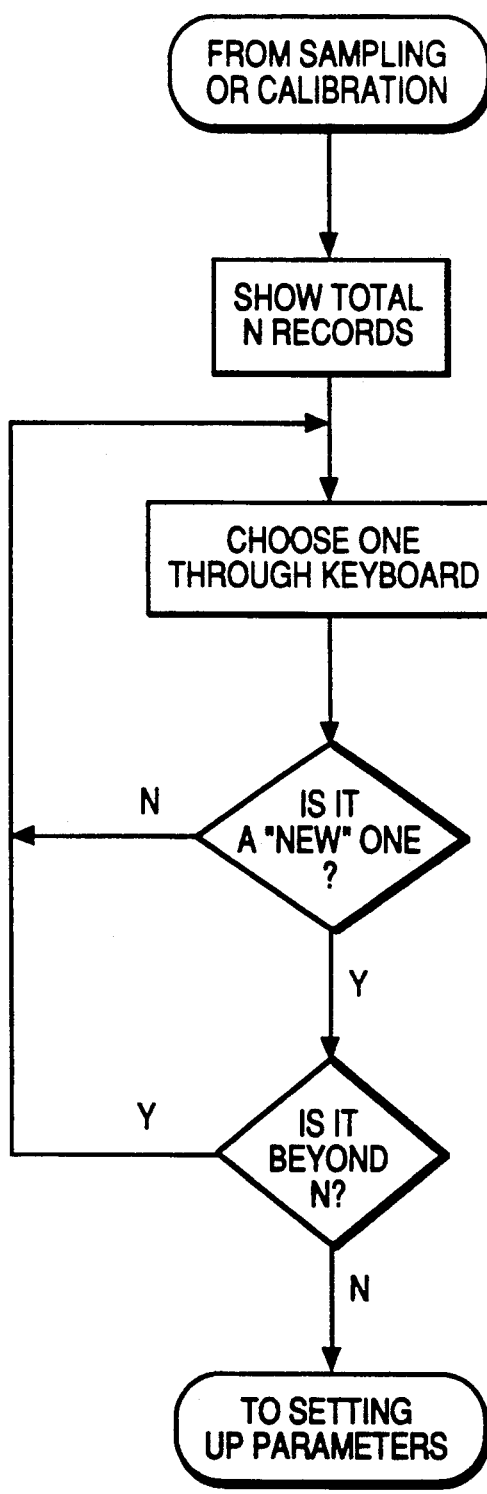
FIG. 8 is a flowchart of a SELECTION routine.

The SELECTION routine flowchart is shown in FIG. 8. The record chosen must be a "new" one, that is one which has not been processed before. This selected record is used in the subsequent software routines.

The hybrid model of the aorta shown in FIG. 1 is based upon the aorta model described in the Welkowitz treatise. The pressures, impedance and aortic flow are all time varying quantities. These parameters are converted or resolved into corresponding Fourier (frequency domain) components. In the frequency domain, transfer function information is derived. By adjusting the values of selected ones of the parameters of the model in the frequency domain, the transfer function of the model is adjusted to match the measured frequency domain transfer function of the subject. The input impedance of the model thereafter also is calculated making use of the parameter values arrived at by the matching procedure. The quotient of carotid pressure and input impedance is then calculated to determine aortic flow in the frequency domain. A retransformation (inverse FFT) is then applied to determine aortic flow in the time domain. Integration of the aortic flow during a single pulse period provides stroke volume. A further multiplication by pulse rate yields cardiac output.

Figure 9:
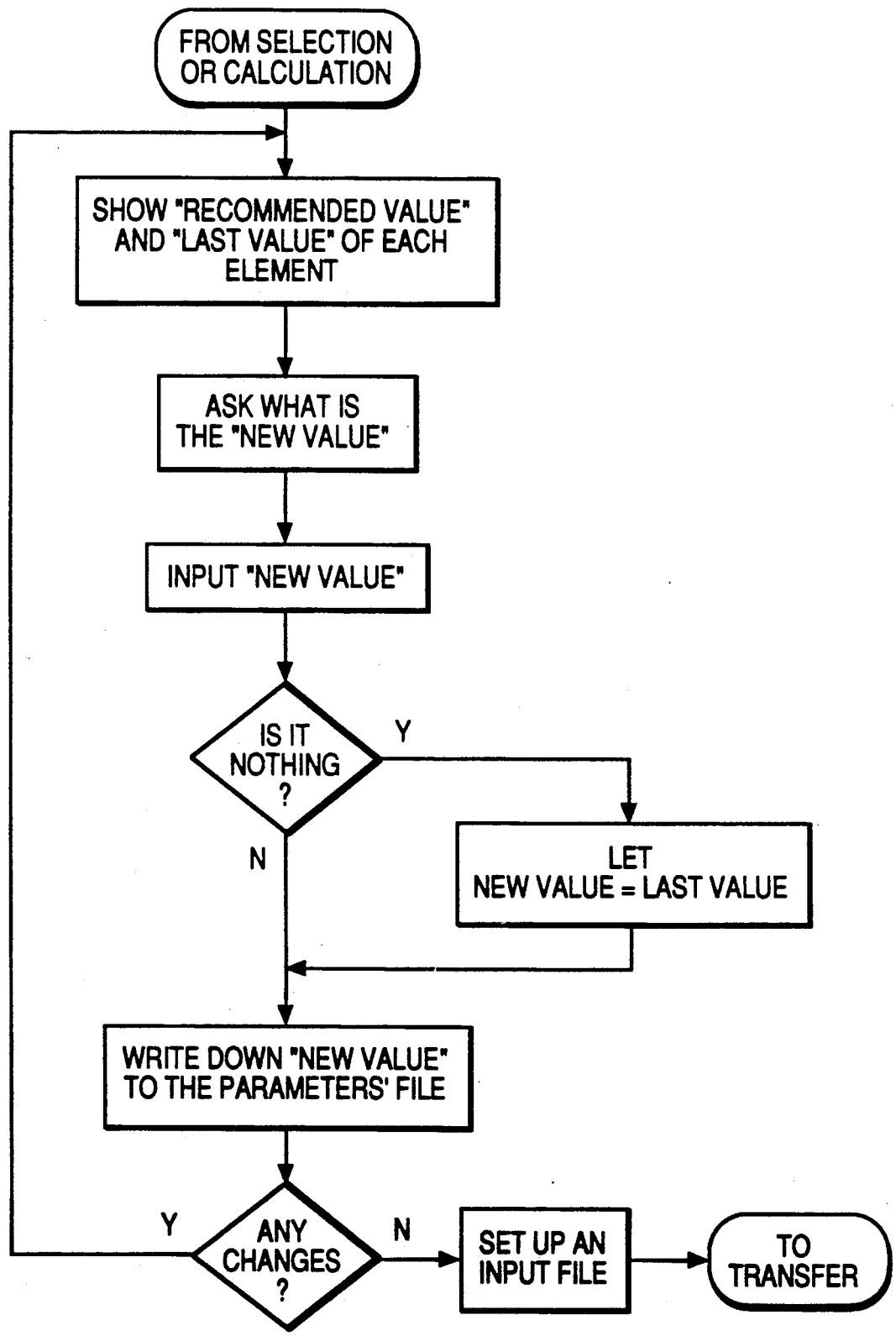
FIG. 9 is a flowchart of a SETTING UP PARAMETERS routine.
Figure 10:
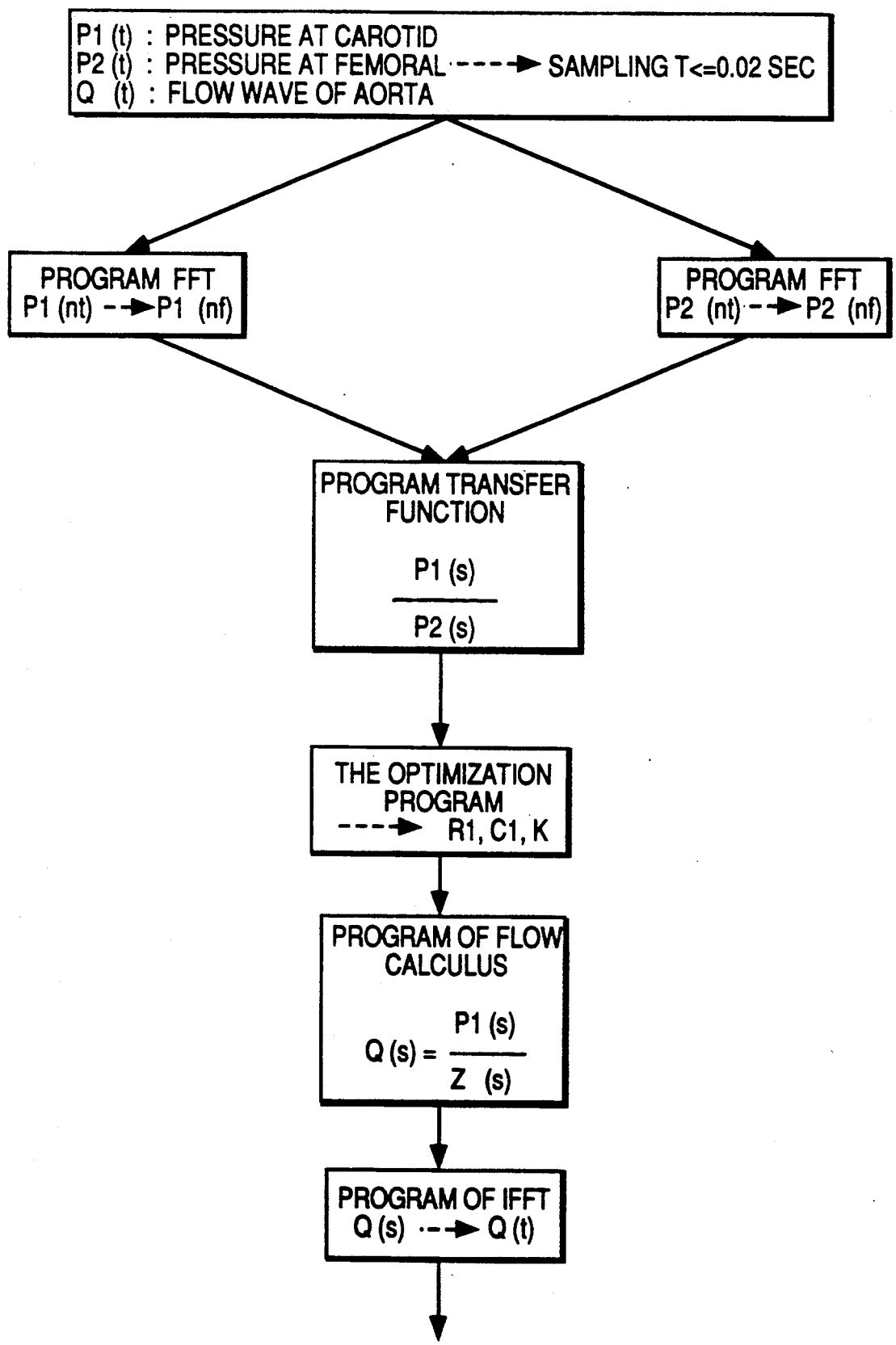
FIG. 10 is a flowchart of a major portion of the programs for determining model parameters.
Figure 11:
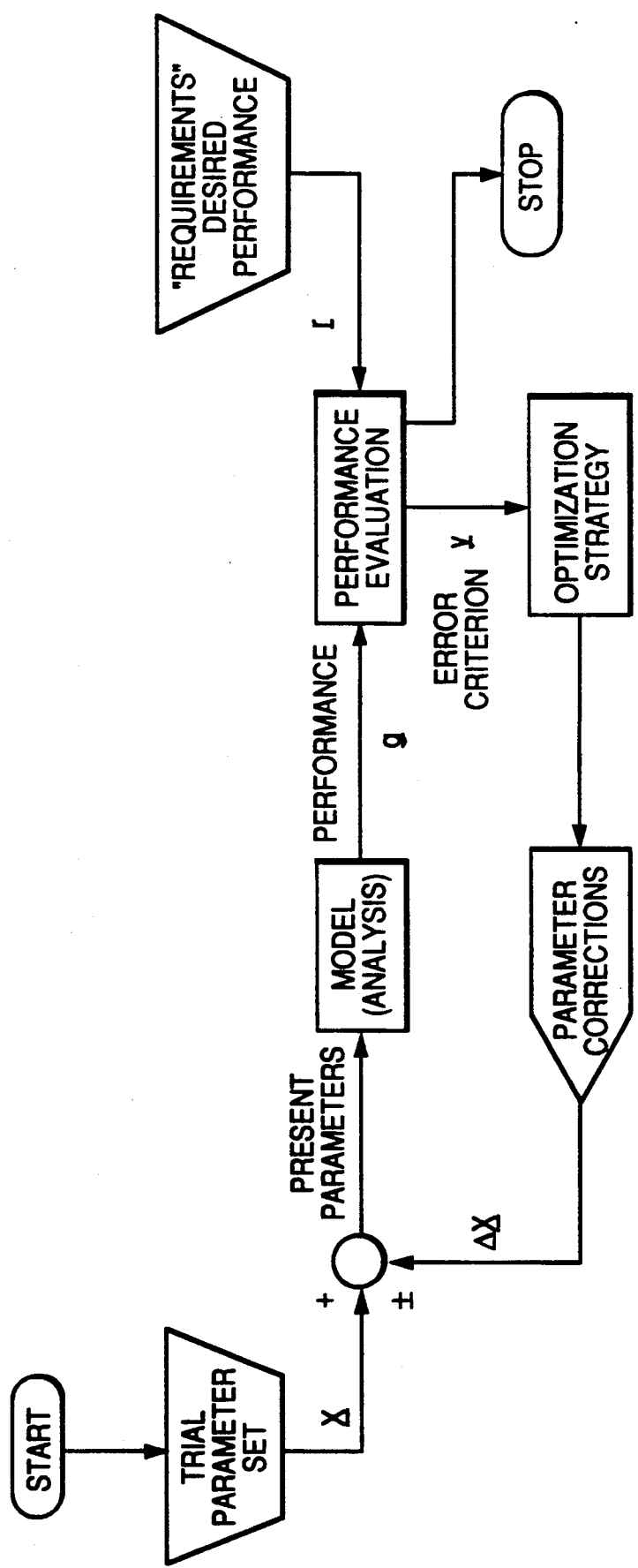
FIG. 11 is a block diagram of an optimization procedure.

In order to begin the process of matching transfer functions of the model and the subject, an initial set of parameters is entered into the model. The SETTING UP PARAMETERS routine flowchart is shown in FIG. 9. The "recommended" values referred to therein are appropriate predicted numbers determined by previous experiments; they provide a good starting point for arriving at a solution in the simulation relatively rapidly. The "last value" is a number adopted in the last preceding case where measurements were taken from the same or a different subject. If no "new value" is chosen, then the "new value" is made equal to the "last value" and saved in a parameters file. However, if a "new value" is chosen, it automatically replaces the "last value" in the parameters file. Using the new set of parameters in the parameters file, the SETTING UP PARAMETERS routine then sets up an initial input file of such parameters for the model. As noted above, the parameter $l_a$ (length of aorta) is normally set at a fixed value of 40 cm, a value which is typical for adults. The sensitivity of the calculation of transfer function to inaccuracies in this parameter are small. However, it is also possible to actually make an external measurement of the distance between the transducers 11 and 12 where desired (e.g., where a child or other non-average size subject is involved) and ato enter the measured value into the program.

The initial set of model parameters are utilized in computer 14 to calculate a pressure transfer function of the model according to the equation for $T_p$ noted above. The pressure transfer function of the model is then compared with that of the subject and an optimization process is commenced. A typical optimization process of this general type is explained in general in the Welkowitz treatise and article cited above. One suitable specific process is illustrated in detail in FIGS. 12-14.

The computer 14 iteratively calculates the model transfer function, compares it to the transfer function of the subject, which was derived from the measured pulse waveforms, determines difference (error) parameters, adjusts the parameters K, R and C selectively to reduce the error and repeats the foregoing process so as to optimally match the calculated transfer function of the model to the measured transfer function of the subject.

In the matching process, a weighted error cost function (see Welkowitz, page 65) is minimized. It has been determined that an acceptable match can be made between the measured and model transfer functions by comparing the first through fifth harmonic amplitude values and the first through third harmonic phase values of the transfer functions. Moreover, the relative influence of the several harmonic components preferably is modified by weighting the errors (difference between measured value and model value) associated with the higher harmonics to a lesser extent than the errors associated with the fundamental or first harmonics.

Suitable weighting factors have been determined to be 1.0, 0.9 and 0.8 for the first, second and third harmonic values, respectively (both phase and amplitude). Weighting factors which have been found to be suitable for the fourth and fifth harmonic amplitude error values are 0.5 and 0.5. The foregoing weighting factors are described in more detail in the Welkowitz treatise in connection with earlier studies performed making use of invasive measuring techniques for dogs and chickens, but such weighting factors have been found to be applicable in connection with the present invention as well.

Figure 12:
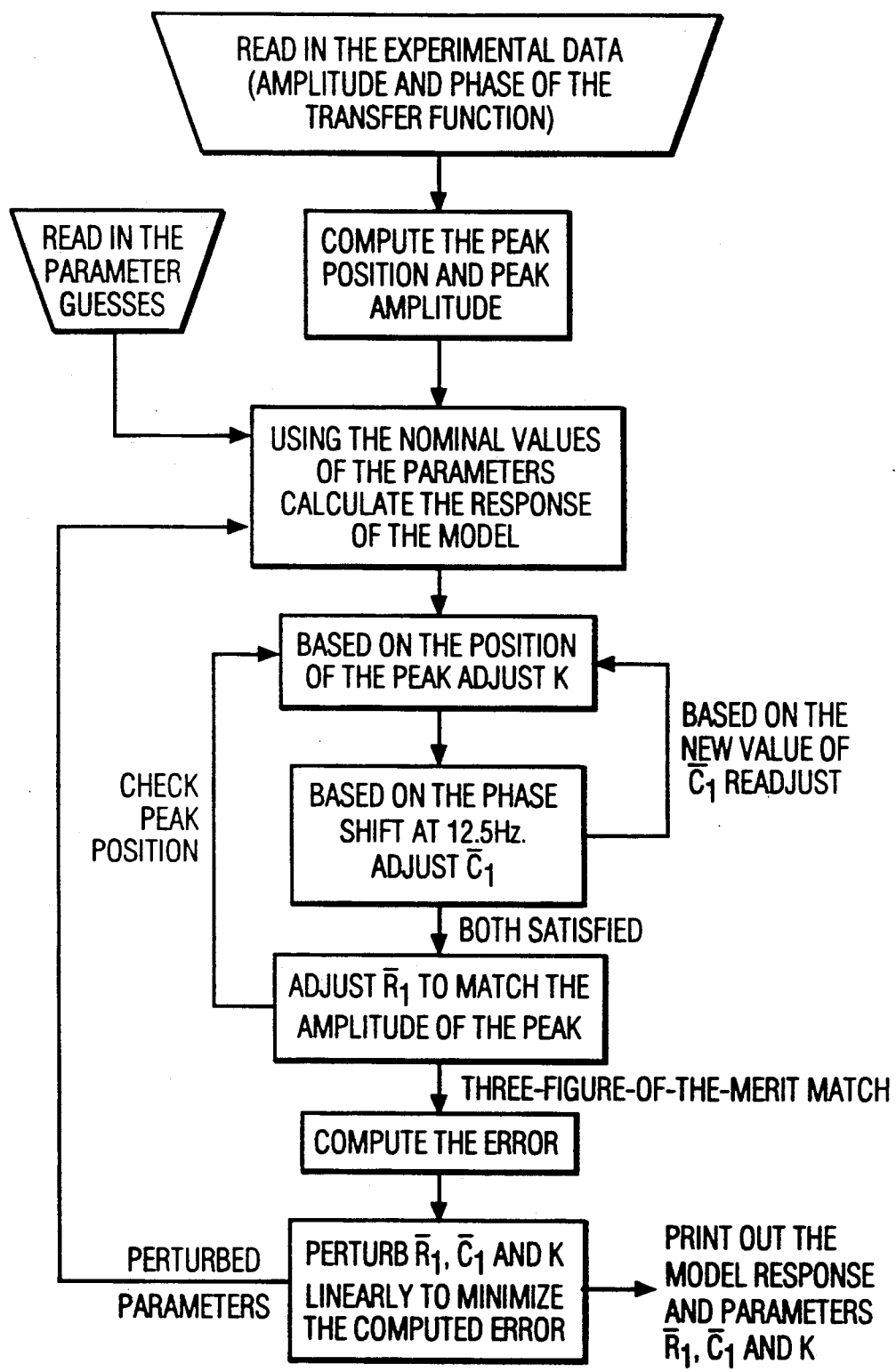
FIG. 12 is a computer flow diagram for a three-figure-of-merit optimization.
Figure 13:
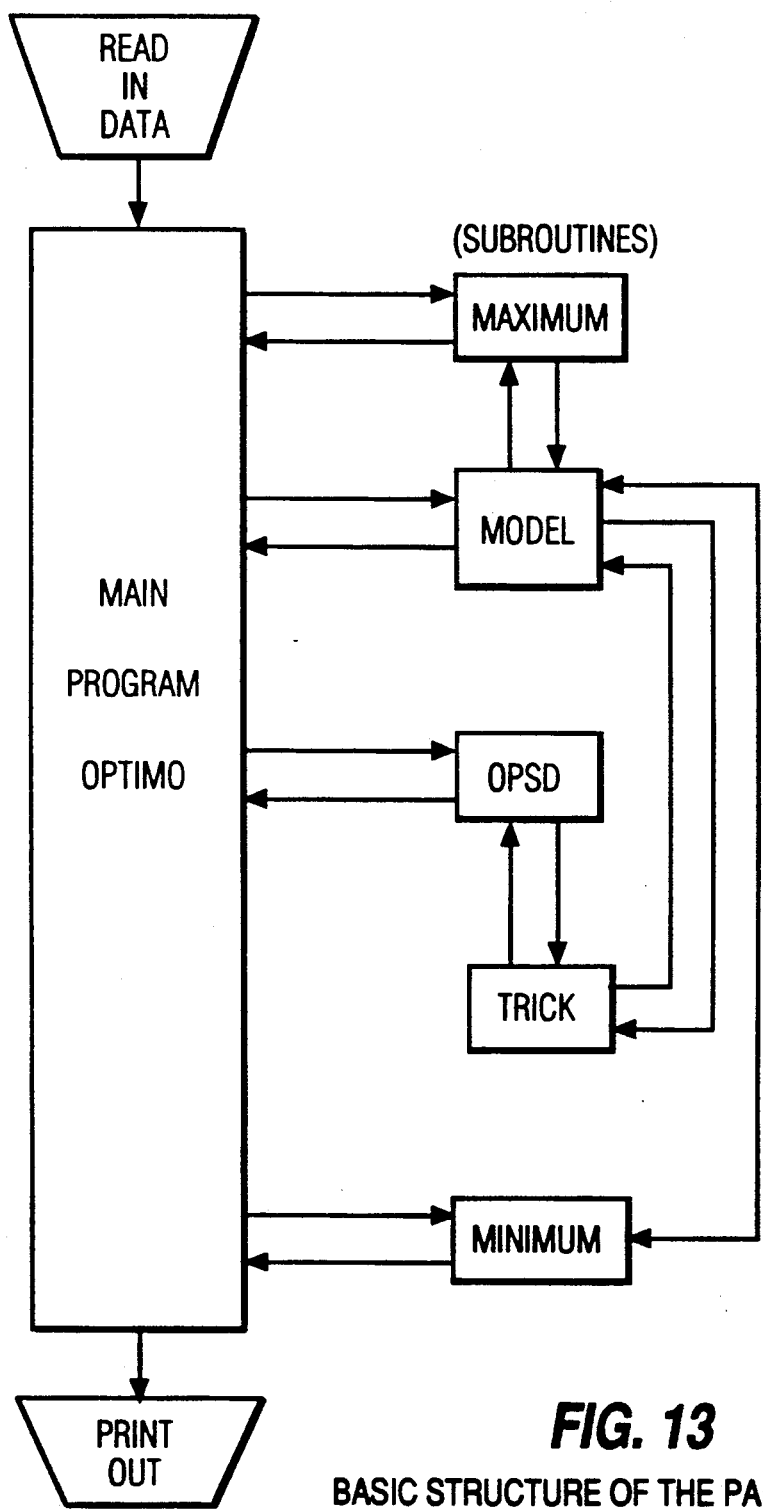
FIG. 13 is a block diagram of the basic structure of a parameter determination program.
Figure 14:
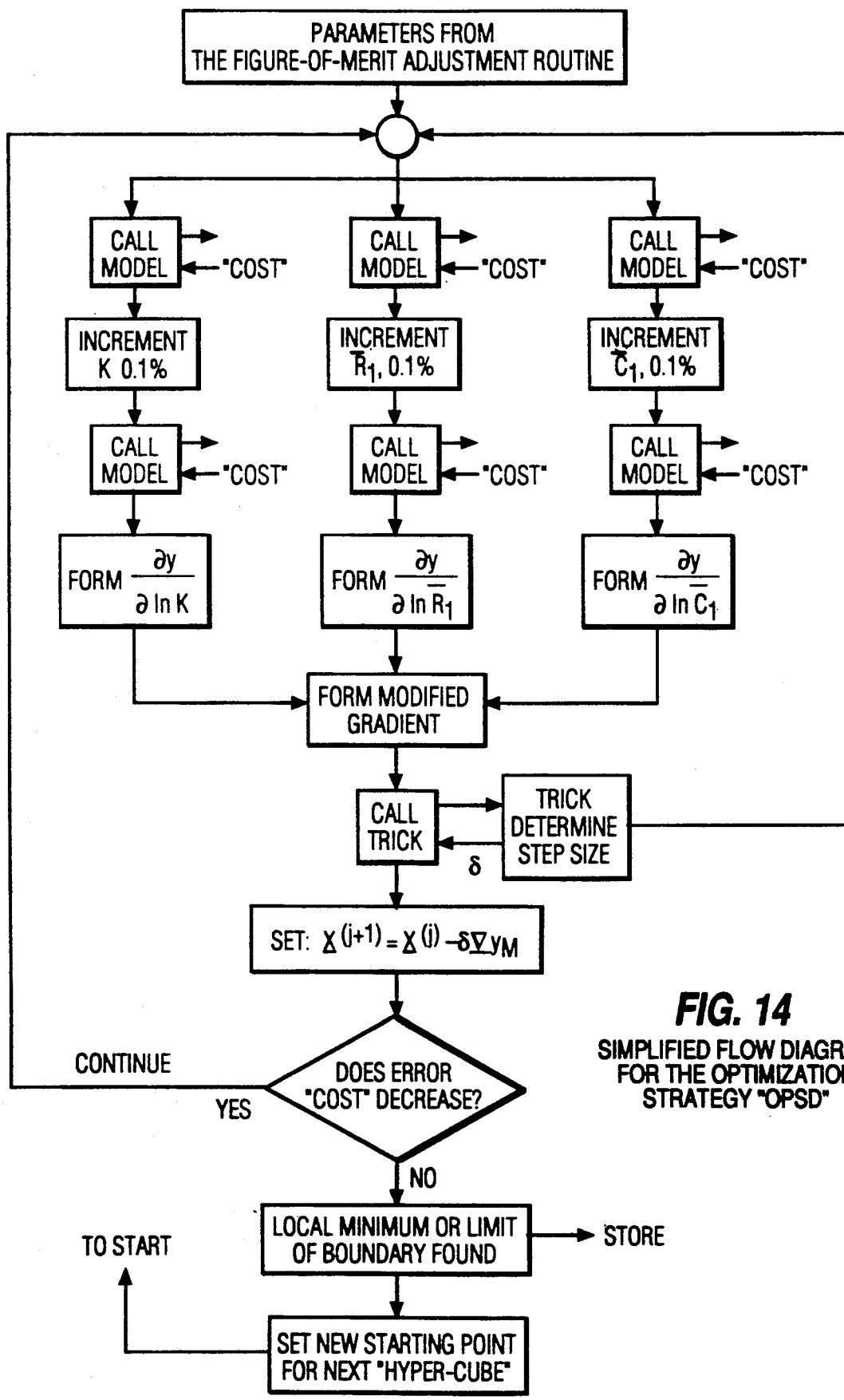
FIG. 14 is a simplified flow diagram for an optimization strategy OPSD.
Figure 15:
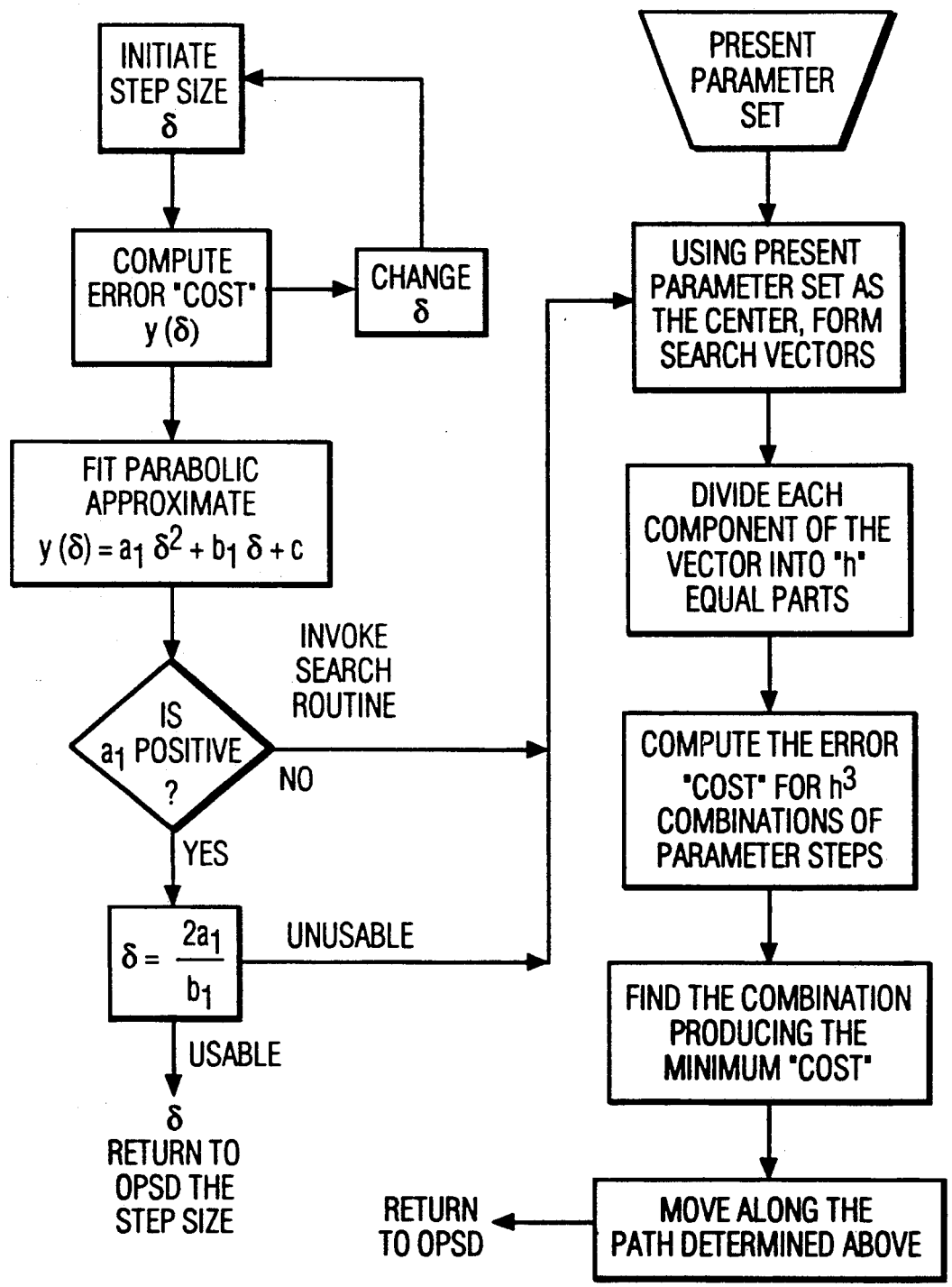
FIG. 15 is a simplified flow diagram of the subroutine "TRICK".

As is shown in FIG. 12, a particularly advantageous approach to matching transfer functions takes into account that adjustment of the parameter K (taper coefficient) will have a significant effect on the position (frequency) corresponding to the peak amplitude response; adjustment of the parameter C (hydraulic capacitance) will have a significant effect on the phase shift at a relatively low frequency such as 12.5 Hertz and adjustment of the parameter R (hydraulic resistance) will have a significant effect on the peak amplitude of the transfer function. Upon reaching the matched condition, the values of the parameters R, C, K and L (blood inertance) of the model have been determined. Those parameters may then be substituted into the equation describing the impedance (Z) of the model to provide stroke volume (Pin/Zin) and total flow information (the integral of stroke volume) regarding the living subject. These calculations preferably are carried out in the frequency domain as well and, thereafter, the flow information is converted to the time domain by an inverse FFT routine.

In the absence of any invasive method of observing aortic flow, it is difficult to determine a "zero" line for the flow waveforms. This is so because of the fact that, in the case of human subjects, there is a small backflow in the aorta between pulses. In the case of the present system, the base line of the calculated time domain flow waveform is adjusted to zero by sampling a number of (e.g., 20) points over an interval of about 400 milliseconds in the region of the minimum amplitude of the calculated flow waveform, averaging the amplitudes of those points and thereafter readjusting the base line of the flow waveform accordingly.

The method and apparatus disclosed provide a simple, fast and inexpensive system for noninvasively determining or monitoring the cardiac output of the living subject being monitored.

Clinical studies have been performed on human subjects to verify the accuracy and usefulness of the methods and apparatus described above. In most cases, the subject was undergoing treatment in a cardiac intensive care unit and was therefore being monitored by means of invasive sensing devices employing a catheter inserted into the aorta. The measurements employing invasive techniques could therefore provide a best case measuring standard against which the performance of the present invention employing non-invasive techniques could be evaluated.

In a typical case, the present invention provided data on blood flow which agreed with that provided by the catheter measurements to within the measuring accuracy of the latter (typically ±10%). It can therefore be stated that the method and apparatus according to this invention are sufficiently accurate that the measurements may be employed for diagnostic and evaluation procedures.

It should also be noted that meaningful information regarding blood flow can be obtained, after determining the equivalent parameters as noted above, by determining average blood flow from the relationship QAVG.=PAVG./ZAVG. where the "average" parameters are defined as the D.C. (zero frequency) components of pressure and impedance in the frequency domain.

While the invention is disclosed in terms of a preferred embodiment, it is not intended that the invention be limited to the described embodiment. It will be recognized by those skilled in the art that modifications may be made without departing from the scope and spirit of the invention. Thus, it is intended that the appended claims cover all equivalent variations as may be subsequently contemplated.

What is claimed is:

1. Apparatus for noninvasively monitoring cardiovascular system parameters of a living subject comprising:

means for sensing a first time varying pulse waveform in the vicinity of the carotid artery externally of the body of the subject and for converting the first pulse waveform to a first time varying electrical representation;

means for sensing a second time varying pulse waveform in the vicinity of the femoral artery externally of the body of the subject and for converting the second pulse waveform to a second time varying electrical representation;

means for digitizing said first and second time varying representations;

means for providing diastolic and systolic blood pressure measurements sensed externally of the body of the subject;

a digital signal processor having means for receiving said digitized first and second time varying representations and said measured blood pressure parameters and for calibrating said first and second digitized representations to provide first and second sets of time varying blood pressure representations, said processor further comprising means for converting said first and second sets of time varying blood pressure representations by Fast Fourier Transform to first and second sets of harmonically related blood pressure components in the frequency domain, means for comparing corresponding ones of said components in said first and second harmonically related sets to determine amplitude and phase transfer function components of the portion of the cardiovascular system between said carotid and femoral arteries, means for simulating said portion of said cardiovascular system by a hybrid electrical circuit model having at least three variable parameters, means for determining corresponding amplitude and phase transfer function components of said hybrid model of said portion of said system and for adjusting said parameters of said hybrid model so as to substantially match said transfer functions of said model and said portion of said cardiovascular system, and means for determining cardiac output utilizing said adjusted parameters of said hybrid model and said first set of time varying blood pressure representations.

2. Apparatus according to claim 1 wherein:
said mean for determining cardiac output comprises means utilizing said adjusted parameters for determining the equivalent input impedance of said hybrid model; means for determining blood flow into said model during each pulse interval by dividing carotid blood pressure information by said input impedance and integrating the resultant flow information to determine stroke volume during each pulse.

3. Apparatus according to claim 2 wherein:
said means for determining cardiac output further comprises means for determining heart rate and means for determining the product of heart rate and stroke volume.

4. Apparatus according to claim 3 wherein:
said means for determining blood flow during each pulse interval further comprises means for converting harmonically related blood flow components in the frequency domain to time domain components by Inverse Fast Fourier Transform.

5. Apparatus according to claim 1 wherein said blood pressure calibrating means comprises means for determining peak and minimum pressure to voltage conversion parameters corresponding to said pulse waveform sensed in the vicinity of said carotid artery and wherein said peak pressure to voltage conversion parameter for said carotid pulse waveform is multiplied by a constant greater than unity to provide a corresponding conversion parameter for said pulse waveform sensed in the vicinity of said femoral artery.

6. Apparatus according to claim 5 wherein said constant is substantially equal to 1.06.

7. Apparatus according to claim 1 wherein said means for providing blood pressure parameters measured externally comprises an arm pressure cuff.

8. Apparatus according to claim 1 wherein said hybrid model is described by the pressure transfer equation $$T_p = \frac{P_1(s)}{P_2(s)} = F_1(\gamma l_a) + F_2(\gamma l_a) + F_3(\gamma l_a) + F_4(\gamma l_a) + F_5(\gamma l_a) + F_6(\gamma l_a)$$

and $$\gamma = (k^2 + sR_aC_a)^{\frac{1}{2}}$$

and said at least three variable parameters comprise $R_a$, $C_a$ and $K$.

9. Apparatus according to claim 8 wherein said means for determining corresponding amplitude and phase transfer function components of said hybrid model comprises means for adjusting said three variable parameters according to an error optimization routine so as to substantially match said transfer functions.

10. A method for noninvasively monitoring cardiovascular system parameters of a living subject comprising the steps of:
externally sensing a carotid pulse and a femoral pulse of said subject;
converting said carotid and femoral pulses to respective carotid and femoral pulse electrical voltage waveforms;
digitizing both electrical voltage waveforms;
calibrating said digitized pulse waveforms with respect to amplitude;
subjecting said digitized waveforms to a Fast Fourier Transform by converting to harmonically related frequency components;
comparing amplitude and phase for each pair of carotid and femoral frequency components to derive measured phase and amplitude transfer functions for the subject;
storing in a computer a hybrid mathematical model of a human aorta;
automatically varying, by means of a matching optimization program stored in said computer, at least three predetermined parameters of the model;
deriving corresponding transfer function components of the model and comparing such components to the measured transfer function of the subject after each adjustment until a substantial match of the measured and calculated transfer functions is obtained;
determining the input impedance of the optimized model utilizing the adjusted, matched parameters;
determining aortic flow components from the impedance parameter of the model and the calibrated, measured carotid pressure information of the subject;
converting the aortic flow components to the time domain by Inverse Fast Fourier Transform; and
determining the time integral of the transformed flow information to provide stroke volume.

11. A method according to claim 10 wherein
said step of calibrating said digitized pulse waveforms comprises externally measuring diastolic and systolic blood pressure parameters externally of the body of a subject, determining a pressure to voltage coefficient for said carotid pulse information from said externally measured parameters, multiplying said coefficient by a factor of 1.06 and applying said multiplied coefficient to calibrate said digitized pulse waveform corresponding to said femoral pulse.

12. A method according to claim 10 wherein:
said hybrid mathematical model comprises a hybrid electrical circuit model in which the pressure transfer function is described by the equations:

$$T_p = \frac{P_1(s)}{P_2(s)} = F_1(\gamma l_a) + F_2(\gamma l_a) + F_3(\gamma l_a) + F_4(\gamma l_a) + F_5(\gamma l_a) + F_6(\gamma l_a)$$

and $$\gamma = (k^2 + sR_aC_a)^{\frac{1}{2}}.$$

13. A method according to claim 12 wherein:
said step of automatically varying parameters comprises iteratively selecting different values for the parameters $R_a$, $C_a$ and $K$ so as to substantially match the transfer function of the subject.

14. A method according to claim 10 wherein:
said step of determining the input impedance of the optimized model comprises substituting adjusted optimized values of Ra, Ca and K into the equation:

$$Z_1(j\omega) = \frac{\gamma R_a e^{(\gamma+k)l_a} + \frac{j\omega L_{a0}}{2}(\gamma - k)^2 - \frac{L_{a0}R_aC_a}{2}\omega^2 e^{\gamma l_a}}{(\gamma - k)\left[\gamma e^{(\gamma+k)l_a} - \frac{L_{a0}C_a}{2}\omega_2(e^{\gamma l_a} - 1)\right]}.$$

15. A method according to claim 14 wherein:
said step of determining aortic flow comprises dividing each transformed carotid pressure frequency component by the calculated input impedance of the optimized model to determine aortic flow frequency components, transforming said flow frequency components to the time domain and integrating said transformed flow in the time domain throughout at least one pulse interval to determine stroke volume.

16. A method according to claim 15 wherein:
said step of determining aortic flow further comprises measuring the time interval of at least one pulse waveform.

* * * * *